United States Patent
Li et al.

(10) Patent No.: US 10,226,294 B2
(45) Date of Patent: Mar. 12, 2019

(54) HYBRID STRAIGHT CUP IMPACTOR

(71) Applicant: Greatbatch Ltd., Clarence, NY (US)

(72) Inventors: Jia Li, Fort Wayne, IN (US); Kenton A. Walz, Fort Wayne, IN (US); Jonathan P. Crandall, Fort Wayne, IN (US); Matthew L. Mroczkowski, Fort Wayne, IN (US)

(73) Assignee: Viant AS&O Holdings, LLC, Foxborough, MA (US)

( * ) Notice: Subject to any disclaimer, the term of this patent is extended or adjusted under 35 U.S.C. 154(b) by 226 days.

(21) Appl. No.: 15/202,055

(22) Filed: Jul. 5, 2016

(65) Prior Publication Data

US 2017/0000540 A1 Jan. 5, 2017

Related U.S. Application Data (60) Provisional application No. 62/187,843, filed on Jul. 2, 2015.

(51) Int. Cl.
*A61F 2/46* (2006.01)
*A61B 17/92* (2006.01)
*A61B 17/00* (2006.01)

(52) U.S. Cl.
CPC ............ *A61B 17/92* (2013.01); *A61F 2/4609* (2013.01); *A61B 2017/0069* (2013.01);
(Continued)

(58) Field of Classification Search
CPC .................................................... A61F 2/4609
See application file for complete search history.

(56) References Cited

U.S. PATENT DOCUMENTS 6,875,237 B2 * 4/2005 Dye .................. A61B 17/1746
623/22.21
7,004,946 B2 2/2006 Parker et al.
(Continued)

FOREIGN PATENT DOCUMENTS

EP 2345392 7/2011
EP 2561835 2/2013
(Continued)

OTHER PUBLICATIONS

Tecomet. Straight Cup Impactor, http://www.symmetrymedical.com/straightcupimpactor.html.
(Continued)

*Primary Examiner* — Nicholas Woodall
(74) *Attorney, Agent, or Firm* — Grossman, Tucker, Perreault & Pfleger, PLLC (57) ABSTRACT

An orthopedic impactor device for positioning an orthopedic prosthetic cup implant during a hip replacement surgery is described. The impactor comprises a distal prosthetic cup engagement portion which is separated from a proximal strike plate by an elongated housing and handle. The housing has a length that extends from a proximal housing portion to a distal housing end with an intermediate housing section therebetween. The intermediate housing section comprises spaced right and left side walls that extend upwardly from a bottom wall to an upper opening. A drive train, comprising a connection rod connectable to an orthopedic prosthetic cup, at least partially resides within the elongated housing. The drive train comprises a linkage sub-assembly that transfers rotational movement of a shaft located at the drive shaft proximal end to the connection rod.

16 Claims, 7 Drawing Sheets

(52) U.S. Cl.
CPC .............. *A61F 2002/4627* (2013.01); *A61F 2002/4629* (2013.01); *A61F 2002/4681* (2013.01)

(56) References Cited

U.S. PATENT DOCUMENTS

| | | |
|---|---|---|
| 7,621,921 B2 | 11/2009 | Parker |
| 7,993,348 B2 | 8/2011 | Conte et al. |
| 8,277,457 B1 | 10/2012 | Burgi et al. |
| 8,398,650 B1 | 3/2013 | Burgi |
| 8,535,324 B2 | 9/2013 | Coustance et al. |
| 8,585,709 B2 | 11/2013 | Burgi et al. |
| 8,834,478 B2 | 9/2014 | Turner et al. |
| 8,834,479 B2 | 9/2014 | Aux Epaules et al. |
| 8,870,886 B2 | 10/2014 | Burgi |
| 8,894,660 B2 | 11/2014 | Coustance et al. |
| 8,961,528 B2 | 2/2015 | Burgi |
| 9,017,415 B2 | 4/2015 | Pinot et al. |
| 9,028,502 B2 | 5/2015 | Burgi |
| 9,119,731 B2 | 9/2015 | Burgi et al. |
| 2007/0156155 A1 | 7/2007 | Parker |
| 2010/0106159 A1 | 4/2010 | Burgi |
| 2013/0261632 A1 | 10/2013 | Livorsi et al. |
| 2014/0114321 A1 | 4/2014 | Davenport et al. |
| 2015/0018833 A1 | 1/2015 | Crandall et al. |
| 2015/0094728 A1* | 4/2015 | Rhoades ............... A61F 2/4609 606/91 |
| 2016/0135963 A1 | 5/2016 | Kerboul |
| 2017/0304078 A1* | 10/2017 | Chenaux ............... A61F 2/4609 |

FOREIGN PATENT DOCUMENTS

| | | |
|---|---|---|
| EP | 2572679 | 3/2013 |
| FR | 2900328 | 11/2007 |
| WO | 2016/055851 | 4/2016 |

OTHER PUBLICATIONS

Extended European Search, Application 16177759.4, dated Nov. 24, 2016.

* cited by examiner

HYBRID STRAIGHT CUP IMPACTOR

CROSS-REFERENCE TO RELATED APPLICATION

This application claims priority from U.S. Provisional Patent Application Ser. No. 62/187,843, filed Jul. 2, 2015.

FIELD OF THE INVENTION

The present invention is directed to minimally invasive surgery, and more particularly to an acetabular prosthetic cup impactor tool for use in minimally invasive hip replacement surgery.

BACKGROUND OF THE INVENTION

A total hip replacement is a reconstructive surgical procedure typically performed by an orthopedic surgeon. A total hip replacement involves placement of an acetabular cup within a patient's acetabular socket and replacement of the patient's femoral neck with a prosthesis which terminates in a ball specifically designed to be positioned in the acetabular cup. Other surgical procedures may require the application of an acetabular cup or other device applied to a patient.

For example, during such acetabular cup procedures, the patient's acetabular socket is reamed out by the surgeon so as to create an enlarged recess to receive the acetabular cup. After the acetabular socket has been reamed, the cup is inserted into the recess and adjusted as necessary to the proper angular orientation. Once deployed, the cup provides a new socket and lining for the patient's acetabulum.

Insertion and placement of the cup by the surgeon is effected either by hand or use of a hand tool that grips the cup. Once the cup is properly positioned in the acetabulum, the cup can be fixed in the desired location by various means such as bone screws, medically acceptable adhesives, or combinations thereof. In many instances, the fixation means include passing bone screws through the cup and into pre-drilled screw holes in the pelvic bone. The bone screws, which are optional, serve to hold the acetabular cup in the acetabulum until bone ingrowth provides permanent fixation.

In one acceptable medical method, the cup is properly positioned in the acetabulum by implantation. One conventional implantation method is to impact an acetabular cup into place after obtaining proper alignment. While impacting the acetabular cup, the surgeon listens for a change in pitch as the cup seats down. The surgeon then probes screw holes to determine if a gap between the cup and the bone is present. If a gap is present, the surgeon further impacts the cup into the acetabulum.

Figure 1:
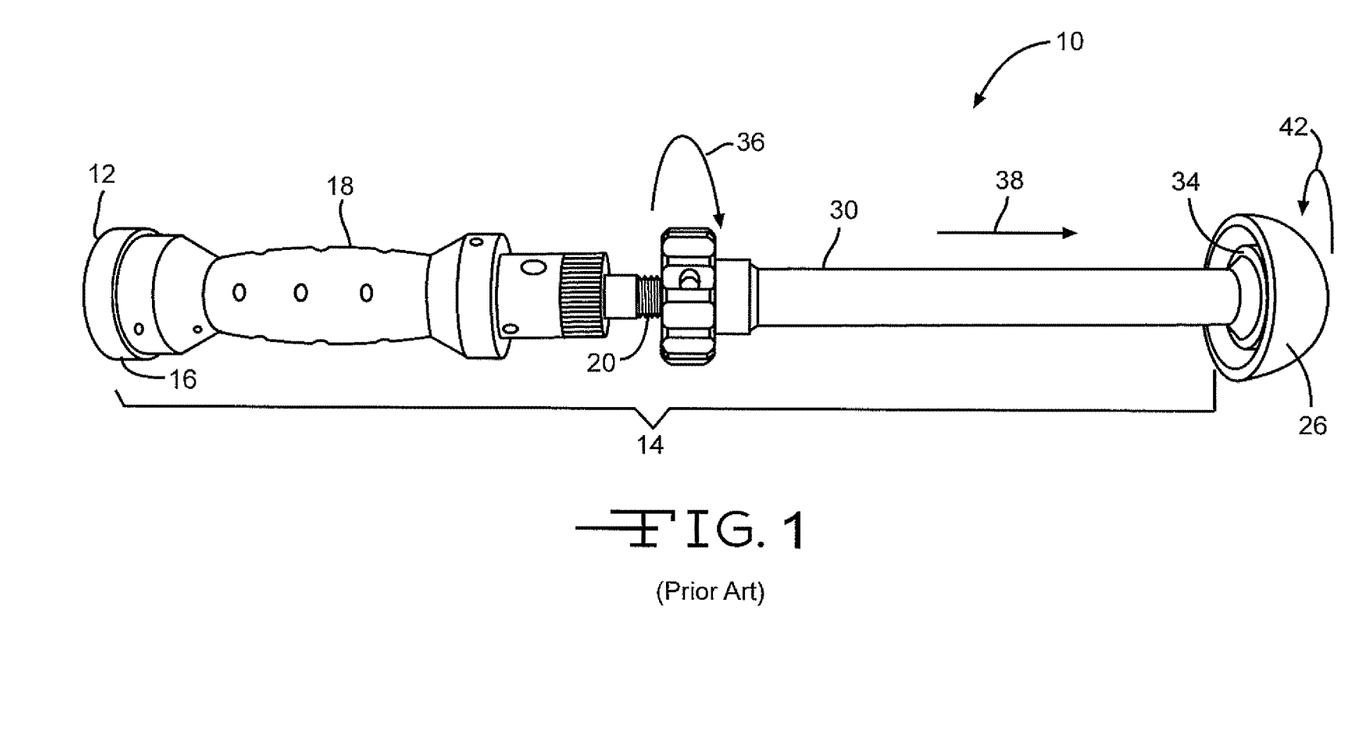
FIG. 1 illustrates an embodiment of a prior art orthopedic cup impactor.
Figure 2:
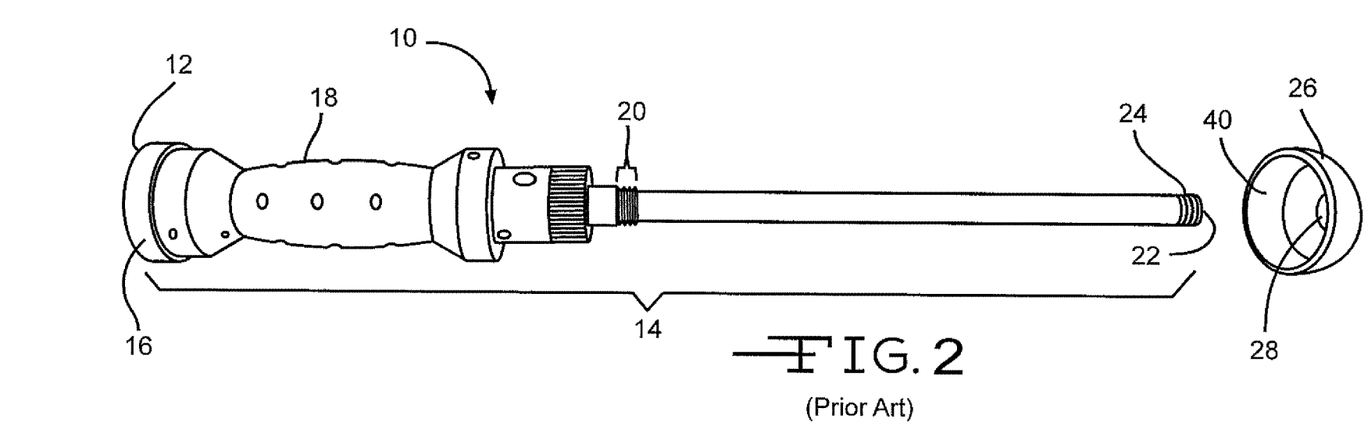
FIG. 2 shows the handle 18 and connected body portion 14 of the prior art impactor shown in FIG. 1.
Figure 2A:
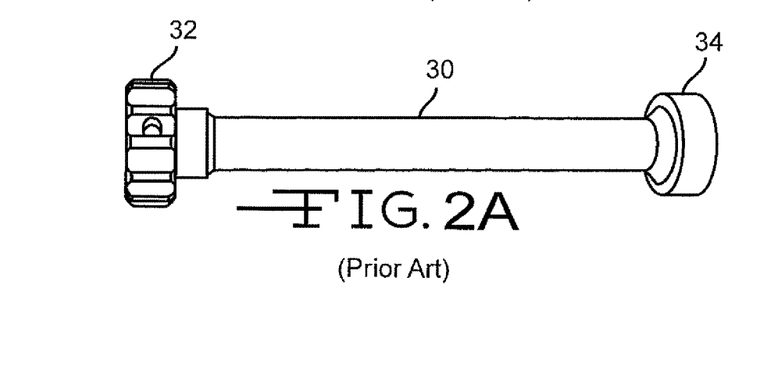
FIG. 2A illustrates the prior art handle device 30 of FIG. 1.

FIGS. 1, 2 and 2A illustrate a conventional spindle-type orthopedic surgical impactor 10. As shown, this prior art impactor 10 has a strike plate 12 that is integrally connected to a proximal end 16 of the impactor body 14. Extending from the strike plate 12 and positioned over a proximal area of the body portion 14 is a fixed handle 18. The fixed handle 18 has a length that allows a surgeon to hold the impactor 10, in one embodiment with one hand, and in an alternative embodiment with two hands. Whatever the fixed handle's 18 length, extending therefrom on the body 14 is an impactor thread section 20. At the body portion's distal end 22 is a tool thread section 24.

The tool thread section 24 threadingly interconnects to a surgical implant device (a.k.a., medical attachment) 26, such as but not limited to an acetabular cup, through a threaded aperture 28 (FIG. 2). That means the implant device 26 is directly connected to the body 14 and the strike plate 12. To ensure the surgical implant device 26 is properly secured to the tool thread section 24, the prior art device 10 uses a rotate handle device 30 (FIG. 2A).

The rotate handle device 30 is positioned in the space between the tool thread section 24 and the impactor thread section 20. At its proximal end, the rotate handle device 30 has a rotating threaded section 32 and at its distal end, an implant support 34. The rotating threaded section 32 has threads that mate with the impactor thread section 20. When the rotating threaded section 32 is rotated clockwise (illustrated by arrow 36 at FIG. 1), (a) the rotating threaded section 32 pushes (illustrated by arrow 38) the rotate handle 30 and the implant support surface 34 toward the surgical implant device's interior surface 40 (FIG. 2); and (b) simultaneously rotates the surgical implant device 26 counter-clockwise (arrow 42 at FIG. 1) through a conventional lock-nut structure of the rotating threaded section 32. This movement results in the surgical implant 26 being pulled toward the implant support 34. Collectively, the clock-wise rotating threaded section 32 is designed to securely position the surgical implant 26 against the implant support 34 to inhibit dislodging of the surgical implant device 26 from the spindle-type tool holder 10 when the surgeon impacts the tool holder.

However, when the surgeon impacts the strike plate 12 there is a possibility that the surgical implant 26 can disconnect from the impactor 10. This could occur when the threaded section 24 or the implant's 26 corresponding threaded section 28 is damaged from the impaction force. Accordingly, what is needed is a firm fixation of the surgical implant 26 during impaction that provides minimal damage to the implant's 26 threads 28. That desired product is achieved with the present invention.

SUMMARY OF THE INVENTION

The prosthetic cup impactor of the present invention comprises a handle assembly located at a proximal impactor end that extends along longitudinal axis A-A to an orthopedic cup engagement end located at a distal impactor end. A drive train comprising a connection rod resides at least partially within a housing that extends lengthwise along longitudinal axis A-A.

The housing has a length that extends from a proximal housing section to a distal housing end with an intermediate housing section therebetween. The intermediate housing section comprises spaced apart right and left side walls that extend upwardly from a bottom wall to an upper opening, thereby forming a housing channel therewithin having a generally U-shaped cross-section perpendicular to a longitudinal axis A-A.

The connection rod, having respective proximal and distal rod ends, is positioned within the housing channel. The distal end of the connection rod is constructed with a threaded end that is designed to threadably attach to a threaded aperture of a prosthetic orthopedic cup. The proximal end of the connection rod resides within the housing channel such that the shaft's proximal end does not contact the inside wall surface at the proximal end of the impactor.

The connection rod proximal end is connected to a shaft located at the drive shaft proximal end. A linkage sub-assembly, comprising a pivot block connected between opposing first and second U-joints, transfers rotational movement of the shaft to the connection rod.

Therefore, because the proximal end of the connection rod is prevented from contacting the inside wall surface at the proximal end of the impactor, the possibility that impaction forces are transferred to the surgical implant through the connection rod is reduced. As a result, the possibility of causing damage to the cup implant, particularly the prosthetic cup's connection mechanism, is reduced.

DETAILED DESCRIPTION OF THE PREFERRED EMBODIMENTS

Figure 3:
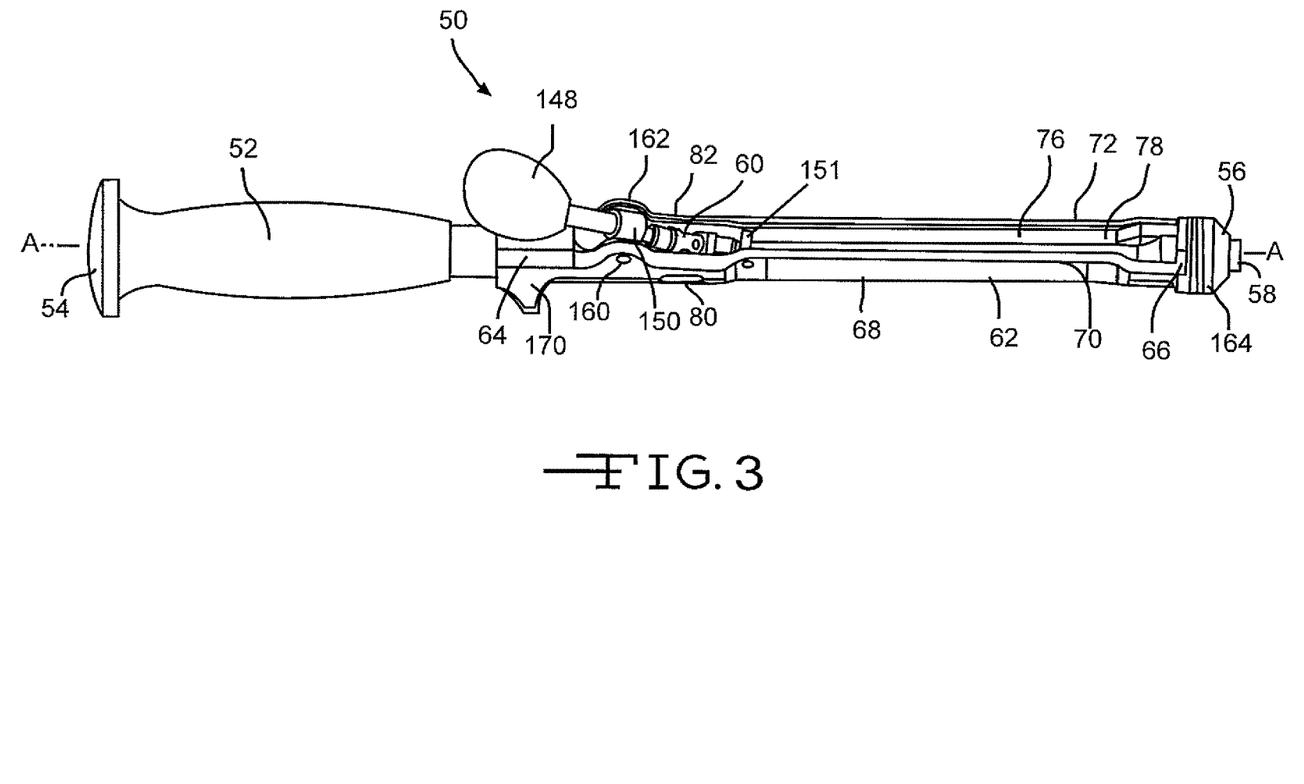
FIG. 3 is a perspective view of the embodiment of the cup impactor illustrated in FIG. 1.
Figure 4:
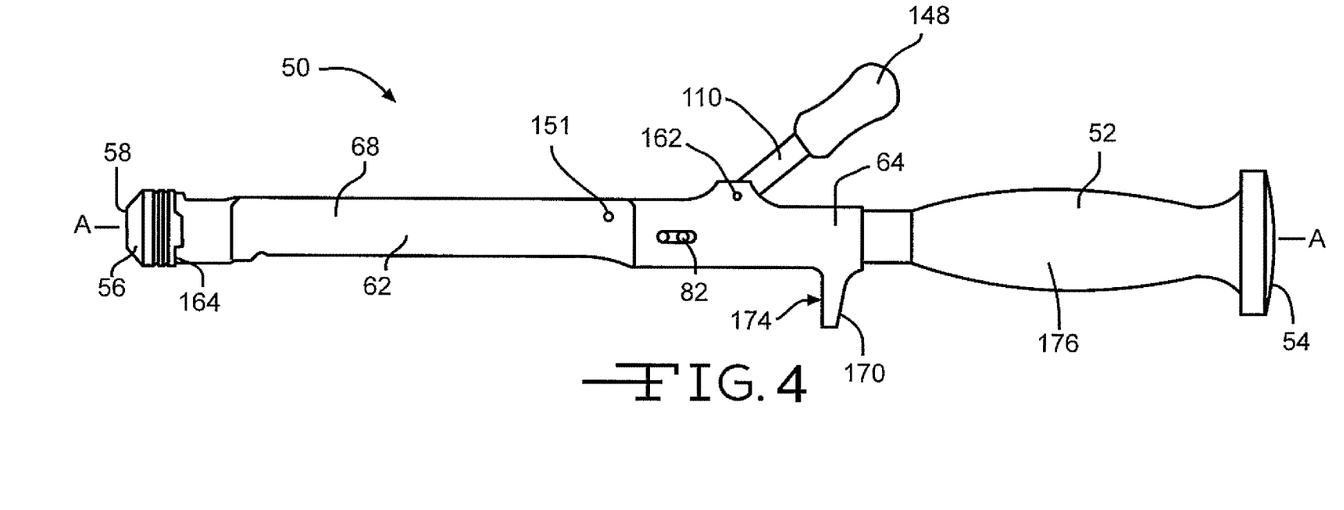
FIG. 4 is a side view of an embodiment of a cup impactor of the present invention.
Figure 5:
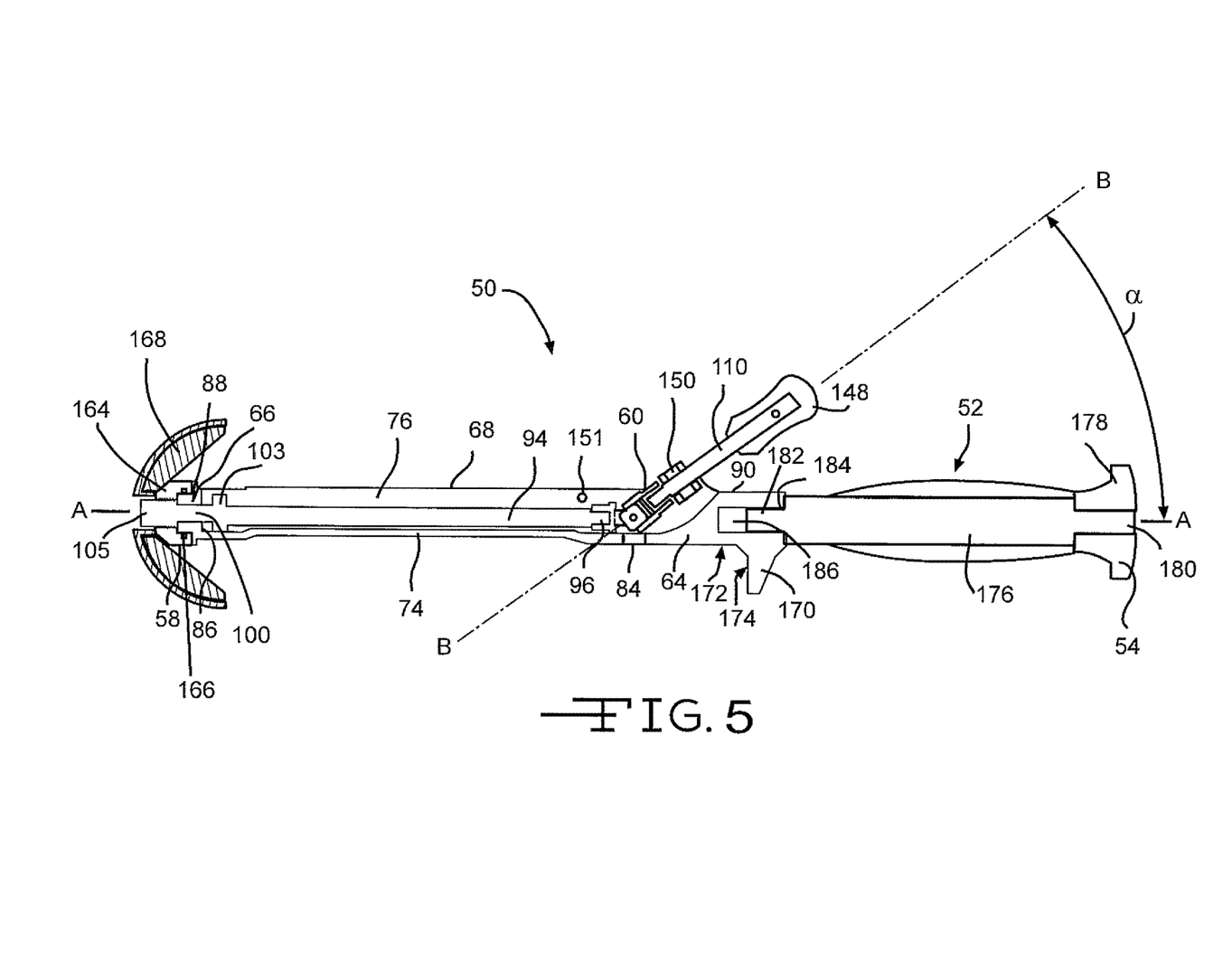
FIG. 5 is a cross sectional view taken along longitudinal axis of the cup impactor of the present invention.

Now turning to the figures, FIGS. 3 to 5 illustrate an embodiment of a cup impactor 50 of the present invention. As shown, the cup impactor 50 comprises a handle assembly 52 located at an impactor proximal end 54. The impactor extends along a longitudinal axis A-A from the handle assembly 52 to a prosthetic cup engagement end 56 located at an impactor distal end 58. A drive train 60 is disposed within a housing 62 that resides between the handle assembly 52 and the cup engagement end 56.

The housing 62 has a length that extends from a housing proximal section 64 to a housing distal end 66 with a housing intermediate section 68 therebetween. The housing intermediate section 68 comprises spaced apart right and left side walls 70 and 72 (FIG. 3) extending upwardly from a bottom wall 74 to an upper opening 76. This construction provides the housing intermediate section 68 with a channel 78 having a generally U-shaped cross-section oriented perpendicular to the longitudinal axis A-A and extending along the length of the housing intermediate section 68 to the distal end 66. A pair of aligned first and second slots 80, 82 extend through the thickness of the respective right and left sidewalls 70, 72 of the housing intermediate section 68. In addition, a third slot 84 (FIG. 5) extends through the thickness of the bottom wall 74. These slots 80, 82, and 84 are designed to allow for efficient and thorough cleaning of the drive train 60 and interior of the housing intermediate section 68.

As illustrated in FIG. 5, the side walls 70, 72 and the bottom wall 74 of the housing intermediate section 68 meet the housing distal end 66 having a partially annularly shaped side wall 86. The annular side wall 86 has a groove 88 with a generally U-shaped cross-section oriented perpendicular to the longitudinal axis A-A. The groove 88 extends lengthwise along the longitudinal axis A-A through the distal housing end 66. The groove 88 is preferably dimensioned such that at least a portion of the distal end of the drive train 60 extends therethrough. The bottom wall 74 slopes in an upward direction meeting a top surface 90 of the housing proximal section 64 at the proximal end of the housing intermediate section 68, As illustrated in FIGS. 3 and 5, the drive train 60 at least partially resides within the housing channel 78 that extends longitudinally to the distal end 66 of the impactor 10. As particularly shown in FIGS. 5 and 7, the drive train 60 comprises a connection rod 94 as a cylindrically-shaped member. The connection rod 94 extends along a length 98 from a proximal end 96 to a distal portion 100 having a distal end 102. The distal rod portion 100 comprises a frustum portion 103 having a base surface 104 that faces the rod distal end 102. The distal rod portion 100 extends to a distal ram portion 105 having a threaded end. The distal portion 100 of the connection rod 94 has a shaft region 107 extending between the frustum portion 103 and the ram 105. This shaft region 107 is positioned within the groove 88 at the housing distal end 66 to thereby permit rotational movement of the shaft while preventing the connection rod 94 from being removed from the housing channel 78.

Figure 6:
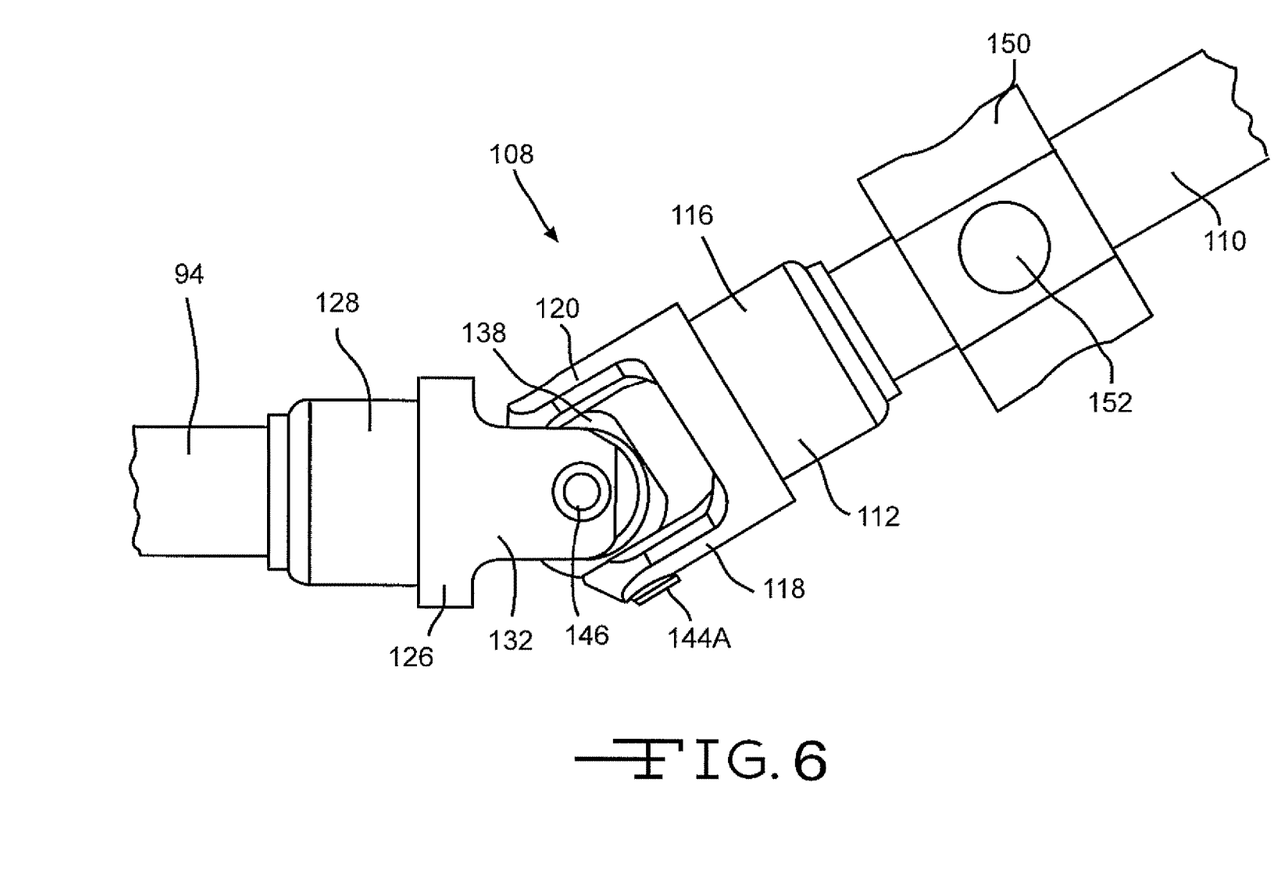
FIG. 6 is a magnified view of an embodiment of the mechanism that joins the rotational rod with the connection rod.
Figure 7:
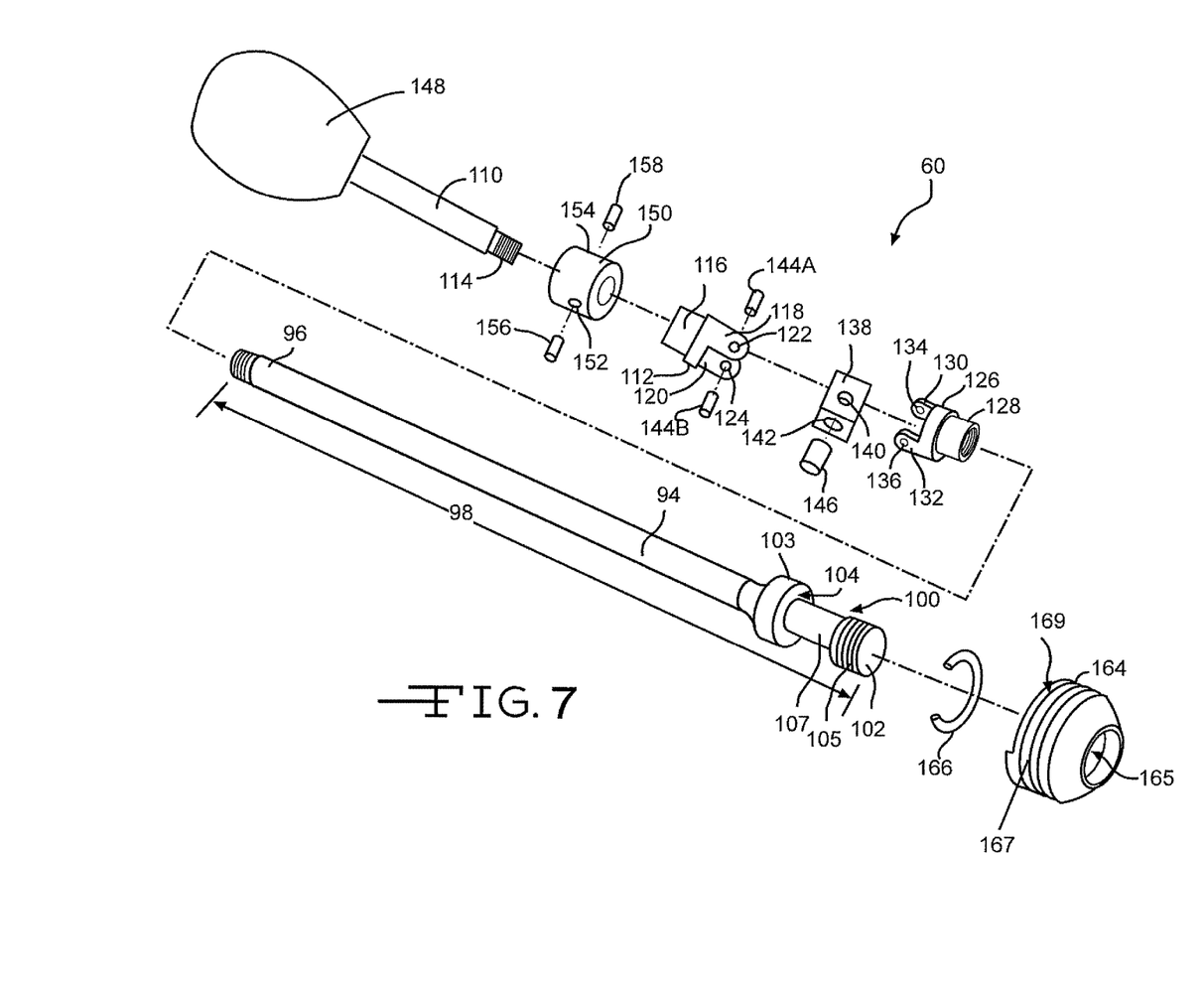
FIG. 7 is an exploded view of an embodiment of the components that comprise the drive train of the present invention.

As particularly shown in FIGS. 6 and 7, a linkage sub-assembly 108 connects the connection rod 94 to a shaft 110 that is positioned at the drive train proximal end. The linkage sub-assembly 108 comprises a first or proximal U-joint 112 that is supported at a distal end 114 of the shaft 110. The proximal U-joint 112 is comprised of a proximal cylindrical side wall 116 supporting a pair of yoke plates 118 and 120 having respective openings 122, 124. Connection of the U-joint 112 to the shaft 110 is made by threading the threaded distal shaft end 114 with corresponding threads that reside circumferentially along an interior surface of the proximal cylindrical side wall 116 (FIG. 7). In the alternative, the proximal U-joint could be welded or otherwise secured in place or, the U-joint and shaft could be machined from a single piece of material.

As shown in FIGS. 6 and 7, the linkage sub-assembly 108 further includes a second or distal U-joint joint 126 that comprises a distal cylindrical side wall 128 supporting a pair of yoke plates 130 and 132 having respective openings 134, 136. A pivot block 138 (FIG. 7) resides between the yoke plates 118, 120 of the proximal U-joint 112 and the pair of yoke plates 130, 132 of the distal U-joint 126. The pivot block 138 comprises two pairs of perpendicularly opposed openings 140 and 142.

Pins 144A, 144B are received in the openings 122, 124 in the yoke plates 118 and 120 of the proximal U-joint 112 and the opening 140 in the pivot block 138, and a pin 146 is received in the opening 142 of the pivot block 138 and the openings 134, 136 of the yoke plates 130, 132 of the distal U-joint 126 to thereby pivotably secure the distal U-joint 126 to the proximal U-joint 112. It is noted that only one of the pins 144 or 146 extends completely from one face of the pivot block 138 to the other face. As passage from one face to the other is blocked by the first pin, the other two pins, either 144A or 144B, are two "half pins".

A knob 148 is preferably connected to the proximal end 96 of the shaft 110. In a preferred embodiment, the knob 148 may be molded over the shaft proximal end 96. Alternatively, the knob 148 may be connected to the proximal end 96 of the shaft 110 in a threaded relationship, welded together, or otherwise secured in place to the proximal shaft end.

A partially cylindrical sleeve 150 is positioned circumferentially around the shaft 110 in an axially slidable relationship therewith. Two diametrically opposed openings 152, 154 that extend through the outer sidewall of the sleeve 150 receive respective screws 156, 158. The screws 156, 158 are positioned through respective aligned openings 160, 162 extending through the left and right side walls 72, 70 of the intermediate section 68 of the housing 62. The respective axes of screws 156, 158 aligned with each other and oriented perpendicular to the longitudinal axis A-A of the connection rod 94. The screws 156, 158 received in the openings 160, 162 provide stability to the shaft 110 as it rotates during a procedure. In addition, a retainer pin 151 (FIG. 3) is preferably positioned extending perpendicular to the longitudinal axis A-A between the right and left sidewalls 70, 72 of the housing intermediate section 68. The retainer pin 151, which is preferably positioned above the connection rod proximal end 96, helps ensure that the connection rod 94 and the linkage subassembly 108 remain within their respective positions within the housing 62.

In a preferred embodiment, illustrated in FIG. 5, shaft 110 is oriented at an angle with respect to longitudinal axis A-A. More specifically, the shaft 110 is oriented at angle α measured between axis B-B extending along shaft 110 and longitudinal axis A-A. In a preferred embodiment, angle α may range from about 20° to about 60°, more preferably, about 45°. This angled orientation of the shaft 110 with respect to the housing 62 provides for an improved line of sight during an orthopedic procedure.

In this manner, the drive train 60 comprising the connection rod 94, the proximal U-joint 112, the pivot block 138, the distal U-joint 126, and the shaft 110 provides for transmission of rotational motion from the proximal end of the connection rod 94 to the distal end 102 of that rod 94.

The threaded ram 105 of the distal portion 100 of the connection rod 94 resides distal of the groove 88 in the annular sidewall 86 of the housing distal end 66. At least partially extends a portion of the threaded ram 105 distal of an orthopedic cup nose 164. The cup nose 164 has a frusto-conical shape and is positioned at the housing distal end 66. In addition, the orthopedic cup nose 164 may comprise a plurality of spaced apart ribs 167 (FIG. 7) positioned circumferentially around and extending outwardly from an exterior surface 169 thereof. A retainer ring 166 may be circumferentially positioned around the housing distal end 66 to help secure the orthopedic cup nose 164 thereto. The threaded ram 105 extends through an opening 165 in the nose 164 in order to engage with an orthopedic implant 168. Prior to a surgical procedure, a connection between the threaded ram 105 and the orthopedic implant 168 is established. In a preferred embodiment, the threaded ram 105 is mated with corresponding thread (not shown) of the implant 168, which is similar to the threaded aperture 28 of the implant 26 shown in FIG. 2. Once the implant is secured to the distal end 58 of the impactor 50, the implant 168 is inserted into a patient. Once the implant 168 is correctly positioned within the body, the connection rod 94 is rotated in a reverse direction with respect to the threads of the ram 105. Typically, the ram 105 is provided with right hand threads so that counterclockwise rotation disengages the implant 168 from the impactor 50.

In a preferred embodiment, as illustrated in FIGS. 3-5, the housing proximal section 64 comprises a kick plate 170. As shown, the kick plate 170 extends outwardly from a bottom surface 172 of the housing proximal section 64. In an embodiment, the kick plate 170 comprises a kick plate surface 174 that faces the distal end 58 of the impactor 50 and is oriented about perpendicular to longitudinal axis A-A. In a preferred embodiment, the kick plate surface 174 may be struck thereby imparting a force thereto so that the impactor 50 may be extracted from a patient during a prosthetic implant procedure in the unlikely event that the impactor 50 becomes immobilized therewithin.

As previously mentioned, the handle assembly 52 is connected to the housing proximal section 64. In a preferred embodiment, the handle assembly 52 comprises a handle 176 and an impaction plate 178 that resides at a proximal end 180 of the handle 176. A post 182 that extends longitudinally from a distal end 184 of the handle 176 is received and secured within an opening 186 extending axially part way into of the housing proximal section 64.

While the preferred embodiments of the impactor and methods have been described in reference to the environment in which they were developed, they are merely illustrative of the principles of the inventions. Other embodiments and configurations may be devised without departing from the spirit of the inventions and the scope of the appended claims.

What is claimed is:

1. An orthopedic impactor, comprising:
   a) an elongated housing extending along a longitudinal axis A-A from a housing proximal section to a housing distal end, wherein a prosthetic cup engagement portion is located at the housing distal end;
   b) a handle connected to and extending proximally from the housing proximal section;
   c) a drive train at least partially disposed with the housing and within the housing, the drive train extending from a drive train proximal end to a drive train distal end, the drive train comprising a connection rod that extends along longitudinal axis A-A from a connection rod proximal end to a connection rod distal portion having a ram distal end at the drive train distal end, wherein the ram distal end is detachably connectable to an orthopedic prosthetic cup;
   d) a kick plate, wherein the kick plate extends outwardly from an exterior surface of the housing proximal section, wherein the kick plate comprises a kick plate surface that faces the impactor distal end; and
   e) wherein rotation of the connection rod at the drive train proximal end causes a connected orthopedic prosthetic cup to travel in an axial direction along longitudinal axis A-A.

2. The orthopedic impactor of claim 1, wherein the drive train comprises a linkage sub-assembly that connects the connection rod proximal end to a shaft having opposed distal and proximal shaft ends, the shaft distal end connected to the connection rod proximal end at the drive train proximal end, wherein the linkage sub-assembly transfers rotational movement of the shaft to the connection rod.

3. The orthopedic impactor of claim 2, wherein the linkage sub-assembly comprises a pivot block that is connected between opposed first and second U-joints.

4. The orthopedic impactor of claim 2, wherein the shaft is oriented at an angle α that is measured between an imaginary axis B-B that extends along a length of the shaft and the longitudinal axis A-A.

5. The orthopedic impactor of claim 4, wherein the angle α ranges from about 20° to about 60°.

6. The orthopedic impactor of claim 2, wherein a knob is connected to the shaft proximal end.

7. The orthopedic impactor of claim 1, wherein a strike plate is located at the handle proximal end.

8. The orthopedic impactor of claim 1, wherein a channel having a generally U-shaped cross-section oriented perpendicular to the longitudinal axis A-A is formed within and extends along a length of the housing intermediate section.

9. The orthopedic impactor of claim 1, wherein a groove having a generally U-shaped cross-section is oriented perpendicular to the longitudinal axis A-A and extends lengthwise along longitudinal axis A-A through the housing distal end, wherein the groove is dimensioned to receive at least a portion of the connection rod distal portion.

10. The orthopedic impactor of claim 9, wherein the connection rod distal portion comprises a shaft region that extends between a frustum portion positioned proximal of the ram distal end, wherein the shaft region is received within the groove that extends through the housing distal end.

11. The orthopedic impactor of claim 1, wherein the connection rod distal portion comprises a frustum portion having a base surface that faces the rod distal end.

12. The orthopedic impactor of claim 1, wherein the ram distal end is threaded, the ram distal end dimensioned to be received within an aperture of an orthopedic prosthetic cup.

13. The orthopedic impactor of claim 1, wherein the housing intermediate section comprises spaced apart right and left side walls extending upwardly from a bottom wall to an upper opening.

14. The orthopedic impactor of claim 1, wherein the prosthetic cup engagement portion comprises an orthopedic cup nose having a frusto-conical shape, wherein the orthopedic cup nose is connected to the housing distal end.

15. The orthopedic impactor of claim 14, wherein the orthopedic cup nose comprises a plurality of spaced apart ribs that extend outwardly from an exterior surface of the orthopedic cup nose.

16. The orthopedic impactor of claim 14, wherein a retainer ring is positioned between the housing distal end and the orthopedic cup nose.

* * * * *